(12) United States Patent
Paulsen et al.

(10) Patent No.: US 10,416,056 B2
(45) Date of Patent: Sep. 17, 2019

(54) WEAR PROGNOSIS METHOD AND MAINTENANCE METHOD

(71) Applicant: Wirtgen GmbH, Windhagen (DE)

(72) Inventors: Sven Paulsen, Bonn-Bad Godesberg (DE); Stefan Wagner, Bad Honnef (DE); Cyrus Barimani, Konigswinter (DE)

(73) Assignee: Wirtgen GmbH (DE)

( * ) Notice: Subject to any disclaimer, the term of this patent is extended or adjusted under 35 U.S.C. 154(b) by 0 days.

(21) Appl. No.: 14/548,870

(22) Filed: Nov. 20, 2014

(65) Prior Publication Data

US 2015/0149027 A1    May 28, 2015

(30) Foreign Application Priority Data

Nov. 25, 2013   (DE) .......................... 10 2013 112 972

(51) Int. Cl.
| | |
|---|---|
| *E01C 23/088* | (2006.01) |
| *G01N 3/56* | (2006.01) |
| *E01C 23/12* | (2006.01) |
| *E21C 35/00* | (2006.01) |
| *G05B 19/4065* | (2006.01) |
| *G01N 3/58* | (2006.01) |

(52) U.S. Cl.
CPC ............. *G01N 3/56* (2013.01); *E01C 23/088* (2013.01); *E01C 23/127* (2013.01); *E21C 35/00* (2013.01); *G05B 19/4065* (2013.01); *G01N 3/58* (2013.01); *G05B 2219/50308* (2013.01)

(58) Field of Classification Search
CPC ................................ G01N 3/56; E01C 23/088
See application file for complete search history.

(56) References Cited

U.S. PATENT DOCUMENTS

| | | | |
|---|---|---|---|
| 4,006,936 A | 2/1977 | Crabiel | |
| 4,655,634 A | 4/1987 | Loy et al. | |
| 6,201,567 B1 | 3/2001 | Kuroda | |
| 6,887,013 B2 | 5/2005 | Ley et al. | |
| 6,990,390 B2 | 1/2006 | Groth et al. | |
| 7,422,391 B2 * | 9/2008 | Holl ...................... | E01C 23/088 299/1.5 |
| 7,905,682 B2 | 3/2011 | Holl et al. | |
| 8,177,871 B2 | 5/2012 | Soma et al. | |

(Continued)

FOREIGN PATENT DOCUMENTS

| | | |
|---|---|---|
| AT | 382683 B | 3/1987 |
| CN | 101666622 A | 3/2010 |

(Continued)

OTHER PUBLICATIONS

Caterpillar Operation & Maintenance Manual, PR-1000 Pavement Profiler, Jul. 1990, 78 pages.

(Continued)

*Primary Examiner* — Jess Whittington
(74) *Attorney, Agent, or Firm* — Lucian Wayne Beavers; Gary L. Montle; Patterson Intellectual Property Law, PC

(57) ABSTRACT

A wear prognosis method and a maintenance method for an earth working machine are disclosed, along with an apparatus for performing the method. Provision is made that the current wear state of one or more earth working tools is sensed. The residual wear capacity until the wear limit is reached is then ascertained from the current wear state.

17 Claims, 10 Drawing Sheets

(56) References Cited

U.S. PATENT DOCUMENTS

| | | |
|---|---|---|
| 8,386,196 B2 | 2/2013 | Wagner et al. |
| 8,757,730 B2 | 6/2014 | Wachsmann et al. |
| 8,775,099 B2 | 7/2014 | Wagner et al. |
| 2005/0207841 A1 | 9/2005 | Holl et al. |
| 2008/0153402 A1 | 6/2008 | Arcona et al. |
| 2010/0076697 A1* | 3/2010 | Wagner .................. B28D 7/00 702/34 |
| 2013/0035874 A1* | 2/2013 | Hall ...................... B02C 18/00 702/34 |
| 2013/0035875 A1* | 2/2013 | Hall ...................... B02C 18/00 702/34 |
| 2013/0128279 A1* | 5/2013 | Wachsmann ............ E01C 23/01 356/601 |
| 2013/0197820 A1 | 8/2013 | Wagner et al. |
| 2014/0116776 A1* | 5/2014 | Marx ...................... E21B 44/00 175/24 |
| 2014/0324364 A1 | 10/2014 | Wagner et al. |

FOREIGN PATENT DOCUMENTS

| | | |
|---|---|---|
| CN | 101745874 | 6/2010 |
| DE | 3136434 A1 | 3/1983 |
| DE | 3411892 A1 | 10/1985 |
| DE | 3218754 C2 | 11/1985 |
| DE | 3505408 A1 | 8/1986 |
| DE | 3616170 A1 | 3/1987 |
| DE | 3818213 A1 | 11/1989 |
| DE | 10015005 A1 | 10/2001 |
| DE | 10203732 A1 | 8/2003 |
| DE | 102005016346 B3 | 1/2007 |
| DE | 102008045470 A1 | 3/2008 |
| DE | 102010014903 A1 | 10/2011 |
| EP | 1039036 A2 | 9/2000 |
| EP | 1396581 B1 | 3/2004 |
| JP | 941863 A | 2/1997 |

OTHER PUBLICATIONS

ARRA Basic Asphalt Recycling Manual, U.S. Department of Transportation Federal Highway Administration, 108 pages, 2001.

Liang et al., Vision-Based Automatic Tool Wear Monitoring System, Jun. 25-27, 2008, Proceedings of the 7th World Congress on Intelligent Control and Automation, Chongqing, China, pp. 6031-6035.

German Patent Office action dated Jul. 17, 2014, with English translation, in corresponding German Patent Application No. DE 102013112973.0, 8 pp. (not prior art).

European Patent Office Action dated Mar. 10, 2017 in corresponding European Patent Application 14 190 286.6-1614 with English machine translation, 10 pp. (not prior art).

China Search Report dated Oct. 31, 2016 in corresponding China Patent Application No. 2014106819280, 2 pp. (not prior art).

India office action dated Apr. 1, 2019 in corresponding India Application No. 3345/DEL/2014 (not prior art).

* cited by examiner

WEAR PROGNOSIS METHOD AND MAINTENANCE METHOD

BACKGROUND OF THE INVENTION

In the context of road reconstruction by milling, and the removal of mineral deposits with a surface miner (also by milling), the earth working tools that are used, and in particular the milling bits, are subject to a continuous wear process. Replacement is advisable once the tools reach a specific wear state, since otherwise the ongoing process loses efficiency. A distinction must be made here among a variety of wear states that result in replacement of a milling bit or bit holder:

1. Bit replacement because sufficient wear material (in particular carbide metal at the tip) is no longer present. The penetration resistance becomes too high and the efficiency thus decreases (too much frictional loss); the wear is predominantly rotationally symmetrical.
2. Bit holder replacement because the wear limit has been reached (wear occurs on the holder at the contact surface between bit and holder). This wear is usually symmetrical.
3. Rotationally asymmetrical wear on the bit tip and/or bit head due to insufficient rotational movement of the bit during the milling process. The consequences are a poor milling pattern as well as the risk of tool breakage, since the bracing effect of the bit head is lost.
4. The bit holder can furthermore be subject to additional rotationally asymmetrical wear.
5. Bit breakage.

In addition, worn and/or broken bits can result in secondary damage to the bit holders, and worn bit holders can cause secondary damage to the milling drum. Timely replacement of the bit and/or bit holder is therefore necessary and reduces costs. If the bits and/or bit holders are changed too soon, however, this procedure is likewise not optimum in terms of cost, since the bits and bit holders are consumable parts and therefore very cost-intensive. Wear potential that is still available is then not being correctly utilized. The wear state of bits and bit holders has hitherto been assessed by visual inspection by the machine driver. For this purpose the machine operator must shut off the machine (switch off engine and decouple drum from the drive train). He must then open the rear drum hatch so the milling drum can be visually inspected.

The milling drum is then rotated by means of a second drive system so that the entire milling drum can be inspected. The drum inspection task can also be handled by a second operator. The wear state of the bit holders is usually assessed by way of so-called "wear markings." The wear state of the bits can be determined by way of the longitudinal wear and the rotational symmetry of the wear pattern.

Monitoring the wear state of bits and holders is very time-intensive, and is unproductive since nothing can be produced during that time. The overall process is disrupted and availability is thus additionally decreased. In addition, because of the highly subjective nature of the assessment, the risk exists that the wear potential of holders and bits will not be optimally utilized.

DE 102 03 732 A1 (U.S. Pat. No. 7,422,391) discloses an apparatus in which operation can be optimized by monitoring operating states of machine components that participate directly or indirectly in the milling process. Among other factors, the wear state of the bits is also assessed by evaluating a variety of machine parameters and variables. The problem that exists during operation of the milling machine is that the milling process and the substrate itself, whose properties fluctuate considerably, have a large influence on evaluation of the operating state of components.

AT 382 683 B discloses a mining machine in which the cutting drum is monitored in noncontact fashion, using photoelectric barriers that detect the presence of the bits. A quantitative wear evaluation is not possible with this method.

DE 10 2008 045 470 A1 (U.S. Pat. No. 8,386,196) discloses a method for quantitative wear identification. Here the position in space of at least point on the earth working tool is sensed. This measurement result is then compared with a reference value so that the wear on the tool can be sensed quantitatively.

As already mentioned above, the material properties of the substrate being processed change during the working process. In mining, for example, it can happen that while traveling over a deposit of material to be removed, the hardness of the raw material suddenly rises ("hard spot"). Increased wear then occurs on the tools.

In order to avoid damage to the cutting equipment due to unpredictable working conditions, for safety reasons the tools are on occasion switched out too soon.

SUMMARY OF THE INVENTION

An object of the invention is to furnish a method that makes possible an economically optimized working process.

This object of the invention is achieved with a method for wear prognosis for an earth working machine, in particular a road milling machine, a surface miner, or the like, the current wear state of at least one earth working tool, in particular of a bit and/or a bit holder, being sensed. This can be effected, for example, using the method according to DE 10 2008 045 470 A1 (U.S. Pat. No. 8,386,196) described above. From the interim result thereby obtained, according to the invention the residual wear capacity until a predefined wear limit is reached is then ascertained in a further method step. A wear state at which the earth working tool must be replaced is consequently defined. By incorporating local conditions, for example, it is then possible, for example, to ascertain the specific remaining service life of the earth working tool. This yields an optimized working process. In particular, the machine operator can now be given specific information that provides him with data regarding the residual wear capacity of the earth working tool. The result is to prevent timely changing of the earth working tool from being neglected, or to avoid premature changing of the earth working tool with the economic disadvantages associated therewith.

According to a preferred variant of the invention, provision can be made that the remaining working output of the earth working machine until the wear limit of the earth working tool is reached is ascertained from the residual wear capacity based on at least one characteristic value or on the derivation of at least one characteristic value. What is ascertained as the remaining working output can be, for example, the milling output, in particular the mass of material that can still be milled and/or the volume of material that can still be milled and/or the remaining travel distance for the earth working machine or the remaining working time for the earth working machine. These parameters give the machine operator information that can be unequivocally implemented.

An effective wear prognosis can be generated by comparing the current wear state of the earth working tool with a reference value reproducing at least a portion of the earth working tool in the worn state, in order to ascertain the residual wear capacity. The reference value can be, for example, a reference contour (partial contour or complete contour), one or more reference points, a reference volume (partial volume or total volume), or the location or direction of the longitudinal center axis of the earth working tool.

The reliability of the working process is additionally improved when provision is further made that the wear state of several or of all earth working tools of the earth working machine is ascertained; and that the earth working tool exhibiting the least residual wear capacity is taken into account for ascertaining the remaining working output until the wear limit is reached. For example, a few representative earth working tools can be selected so that a detailed wear statement can be made. If all the earth working tools are monitored, an almost one-hundred-percent wear statement becomes possible.

A method according to the present invention for wear prognosis can be characterized in that a working area within which two or more earth working machines are being used is defined; and that the current wear state of at least one earth working tool of an earth working machine is ascertained, and that the at least one characteristic value or the derivation of the one or more characteristic values is derived from the previously produced milling output of said at least one earth working tool and from the wear, corresponding thereto, of the at least one earth working tool. A reference working process is therefore carried out. For example, firstly unworn tools or tools that already exhibit partial wear are used. The working process is then carried out using a working machine of this kind. During this process, various parameters can then be acquired, in particular the milling output produced. The milling output produced can be, for example, as already described above, the mass of material milled, the distance traveled, etc. A correlation can then be arrived at by differential analysis between the previously known wear state and the wear state existing after the working process. This indicates the wear that has occurred on the tools in the context of the working output produced. From this, one or more characteristic values can then be derived. These characteristic values can then be used in order to ascertain, for any given wear state (and residual wear capacity resulting therefrom), the working output still to be produced (for example, until the wear limit is reached).

These characteristic values can correspondingly be ascertained and utilized directly on the working machine that is present, or they can be conveyed to at least one further earth working machine that, in particular, is working a comparable substrate.

In another embodiment of the invention, the at least one characteristic value is ascertained in consideration of the material properties, in particular the abrasiveness and/or material hardness, of the substrate to be worked.

For practical reasons, the at least one characteristic value can be ascertained preferably in consideration of a material hardness range that contains the material hardness of the substrate being worked. Additionally or alternatively, provision can also be made that the characteristic value is ascertained in consideration of an abrasiveness range that contains the abrasiveness of the substrate to be worked. For example, selective measurements from the sector to be worked can be representatively performed, and the values for material hardness and/or abrasiveness can be determined in that context.

In mining it is usual to take samples from an area that is to be worked, in particular to perform sample boring operations. The samples are then investigated and the raw material's parameters are identified. According to an inventive alternative, these results can also be used directly in the method according to the present invention, so that the characteristic values/material properties for inferring the characteristic values can be ascertained therefrom.

It is also conceivable for the machine operator to be able to select, from a list of different substrate categories, the category suitable for the substrate currently to be worked, and for the material properties for ascertaining the at least one characteristic value to be associated with said substrate categories. The result is that the machine operator can simply assess the substrate on site in consideration of his accumulated experience, and can make a corresponding selection. For example, one or more characteristic values are associated with this substrate category in a database. When the substrate category is selected, these characteristic values are then read out from the database and processed via software in order to ascertain the residual wear capacity and thus the remaining working output. This method has the advantage that the machine operator can respectively determine the residual wear capacity and the remaining working output directly on site, and can also implement an adaptation in particular as substrate categories change.

Alternatively or additionally, it is also conceivable to indirectly sense the material properties of the substrate to be worked. Provision can be made here that the material properties for ascertaining the at least one characteristic value are ascertained during working operation on the basis of machine parameters. For example, the milling depth, machine advance, milling drum rotation speed, torque applied to the processing tools, and/or power output currently being delivered by the drive engine can be ascertained. These machine parameters provide information regarding the material properties, in particular the abrasiveness or hardness, of the substrate to be processed. The rotation speed, torque, and delivered power output can be taken directly from the engine control unit (ECU) of the drive engine. The first two parameters can be furnished by the machine control system.

A particularly preferred inventive variant is such that firstly the current wear state and the residual wear capacity are ascertained; and then the working output produced by the earth working machine, in particular the milling output and/or the machine data occurring during that working process, are monitored. The actual wear state of the earth working tool can then be ascertained, for example calculated, continuously during the working process. If, for example, a change in the substrate category then occurs or if a new processing task is undertaken, this most recently ascertained actual wear state can be employed as a current wear state for purposes of the invention, and the residual wear capacity available for the task at hand can then be ascertained.

A calculation unit, with which a memory unit is associated, is preferably provided. The one or several characteristic values, or the derivation of the characteristic values, is/are stored in the memory unit. The current wear state can be sensed with a sensing device. The remaining working output until the wear limit of the earth working tools is reached can be ascertained by means of the calculation unit using the current wear state, the residual wear capacity resulting therefrom, and the characteristic value or values or the derivation thereof. The residual wear capacity can be ascertained in the calculation unit on the basis of the wear state and the reference contour. The calculation unit and/or the memory unit can be, for example, directly associated with the earth working machine. It is also conceivable, however, for the calculation unit and/or the memory unit to be associated with a separate system unit. When provision is made for separate association, the earth working machine can then be in mutual communication with the system unit via a preferably wireless remote data transfer link. Depending on the whereabouts of the earth working machine, the latter can then be supplied with relevant parameters; in particular, the residual wear capacity and/or remaining working output can be conveyed. Among the advantages of this is the fact that when multiple earth working machines are being used in one working area, they can each individually retrieve the necessary data from the system unit.

The characteristic values can be stored in the calculation/memory unit as a function of location. For example, a map of, for example, a mine can be stored, in which map different characteristics values are associated with different locations. The machines can possess GPS, or the operator inputs his location, and the corresponding characteristic values are used. It would also be possible, especially in the context of an external calculation unit, for only the material properties to be stored and for the characteristic values to be ascertained by the machine itself on the basis of those material properties.

The object of the invention is also achieved by a maintenance method for an earth working machine, in which a plurality of earth working tools, in particular bits and/or bit holders, are used. In this context, the current wear state of at least one earth working tool is sensed. Proceeding from that wear state, the residual wear capacity of the earth working tool is then ascertained. Before the wear limit of the earth working tool is reached, a technician is then informed so that maintenance can be carried out. In the context of this maintenance method, a prognosis regarding the remaining milling output can be created in consideration of the residual wear capacity that is ascertained. A maintenance unit can be informed in timely fashion before said milling output has been entirely produced. This can occur, for example, in automated fashion by means of a signaling device of the earth working machine. This signaling device outputs a corresponding signal that can be conveyed preferably wirelessly to a maintenance station. The working output of the earth working machine remaining until the wear limit of the earth working tool is reached can be signaled in the form of the distance that can still be milled, the volume or mass that can still be milled, and/or the remaining service life. In the context of an earth working machine, for example, it is possible for the residual wear capacity of the earth working tool to be ascertained before a planned working process is undertaken. The maintenance intervals for that working process can then already be predicted or optimized in advance as a function of the predicted wear for the milling task.

Whereas the material characteristic values and residual wear capacity can be taken into account in order to ascertain the remaining working output, here conversely the expected bit change is ascertained using the material properties and the remaining working output.

BRIEF DESCRIPTION OF THE DRAWINGS

The invention will be explained in further detail below with reference to an exemplifying embodiment depicted in the drawings, in which.

DETAILED DESCRIPTION

Figure 1:
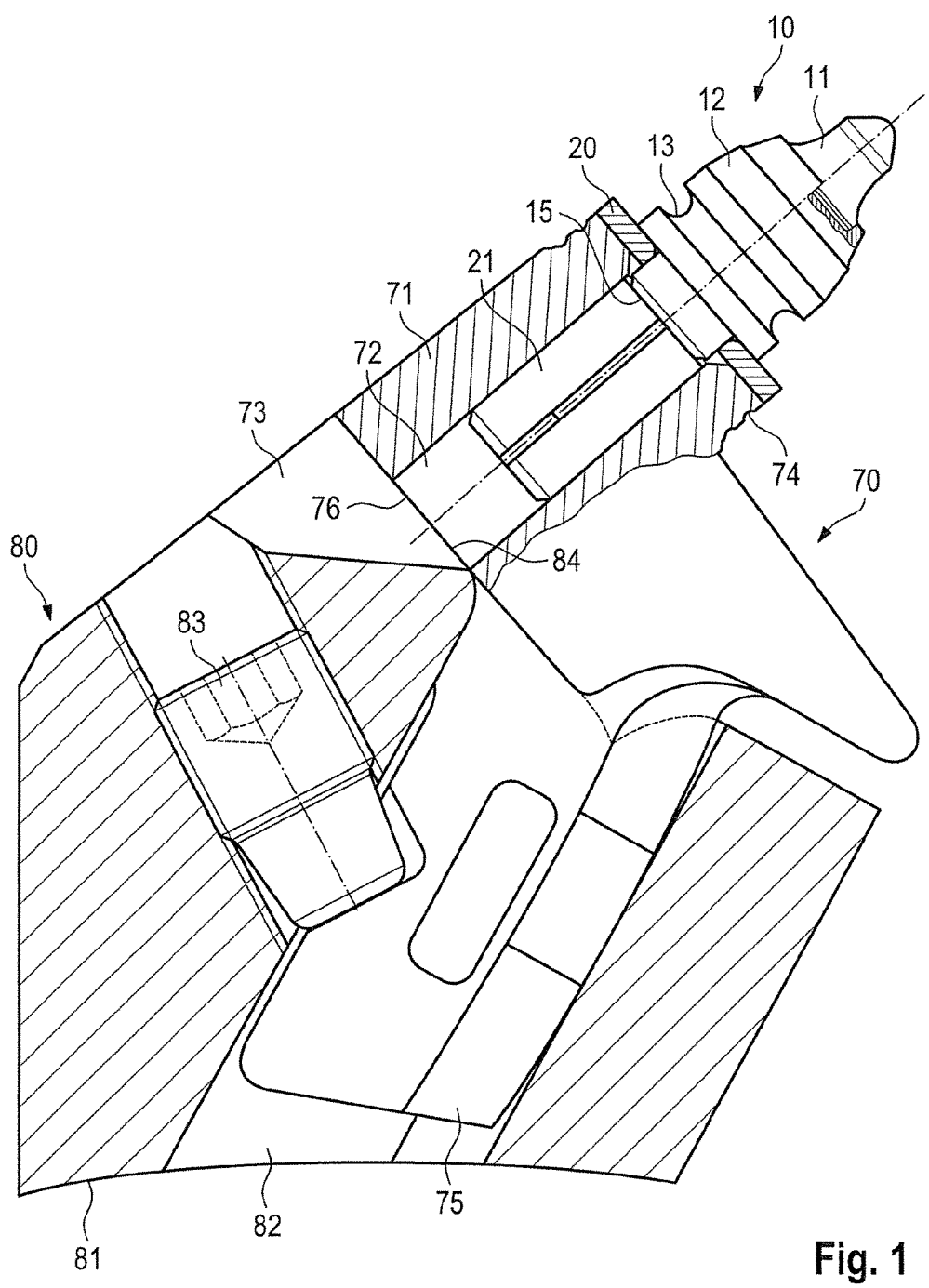
FIG. 1 is a side view of a bit, namely a round shank bit for a road milling machine, a mining machine, a surface miner, or the like, which is inserted into the holder of a quick-change holder tool for such machines.

FIG. 1 shows, as an example of an earth working tool, a bit 10 as known from the existing art and described by way of example in DE 38 18 213 A1. Bit 10 comprises a bit head 12 and a bit shank 15 shaped integrally thereonto. Bit head 12 carries a bit tip 11 made of a hard material, for example of carbide metal.

This bit tip 11 is usually soldered onto bit head 12 along a contact surface. A circumferential pull-out groove 13 is recessed into bit head 12. This groove serves as a tool receptacle, such that a removal tool can be set in place and bit 10 can be removed from a bit holder 70.

Bit shank 15 carries a longitudinally slotted cylindrical clamping sleeve 21. This is held on bit shank 15 in lossproof fashion in the direction of the longitudinal dimension of bit 10, but freely rotatably in the circumferential direction. A wear protection washer 20 is arranged in the region between clamping sleeve 21 and bit head 12. In the installed state, wear protection washer 20 is braced against a countersurface of a bit holder 70 and against bit holder 70, facing away from the underside of bit head 12.

Bit holder 70 is equipped with a projection 71 into which a bit receptacle 72 in the form of a cylindrical bore is recessed. In this bit receptacle 72, clamping sleeve 21 is held with its external periphery clamped against the inner wall of the bore. Bit receptacle 72 opens into a drift opening 73. Through this, a drift punch (not shown) can be introduced for the purpose of removing bit 10. Said punch acts on the end of bit shank 15 in such a way that bit 10 is pushed out of bit receptacle 72 as the clamping force of clamping sleeve 21 is overcome.

As is evident from FIG. 1, extension 71 is equipped in a cylindrical region below wear protection washer 20 with two circumferential grooves. These grooves serve as wear markings 74. During operational use, wear protection washer 20 rotates and, in that context, can create wear (bit holder wear) on the support surface of projection 71. When the support surface has been worn away to the extent that the second wear marking has been reached, bit holder 70 is considered to be worn in such a way that it must be replaced.

Bit holder 70 comprises an insertion projection 75 that is introducible into an insertion receptacle 82 of a base part 80 and can be clamped there by means of a clamping screw 83. Clamping screw 83 presses an abutment surface 76 of bit holder 70 onto a support surface 84 of base part 80. Although this is not depicted in further detail in FIG. 1, base part 80 itself is welded via its underside 81 onto the milling drum tube of a milling drum.

Figure 2:
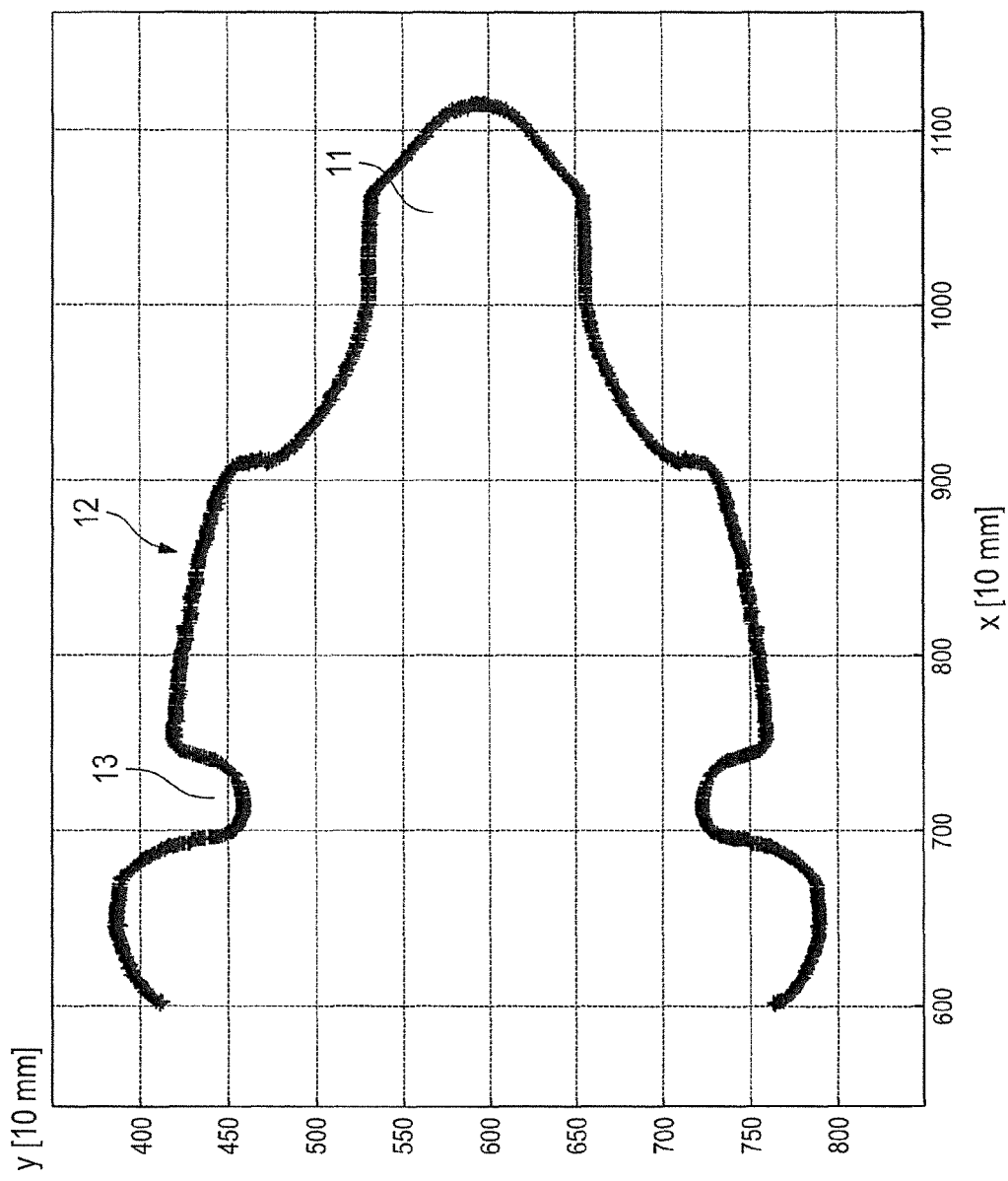
FIG. 2 is a diagram showing the bit head of the bit according to FIG. 1.

Noncontact surveying of bit head 12 is performed in order to ascertain the current wear state of bit 10 installed on the bit holder, a defined point or multiple points of bit head 12 being measured/ascertained as a position value. FIG. 2 is a side view of the contour of an unworn bit head 12. This contour is illustrated in a diagram, the dimension of bit head 12 in the direction of the longitudinal bit axis of bit 10 (X axis) being plotted against the dimension in the width direction (perpendicular to the longitudinal center axis, i.e. Y axis). The contour of bit head 12 (including bit tip 11) is assembled from a plurality of measured points, and the linear boundary (contour line) represents an interpolation of these position values.

Figure 9:
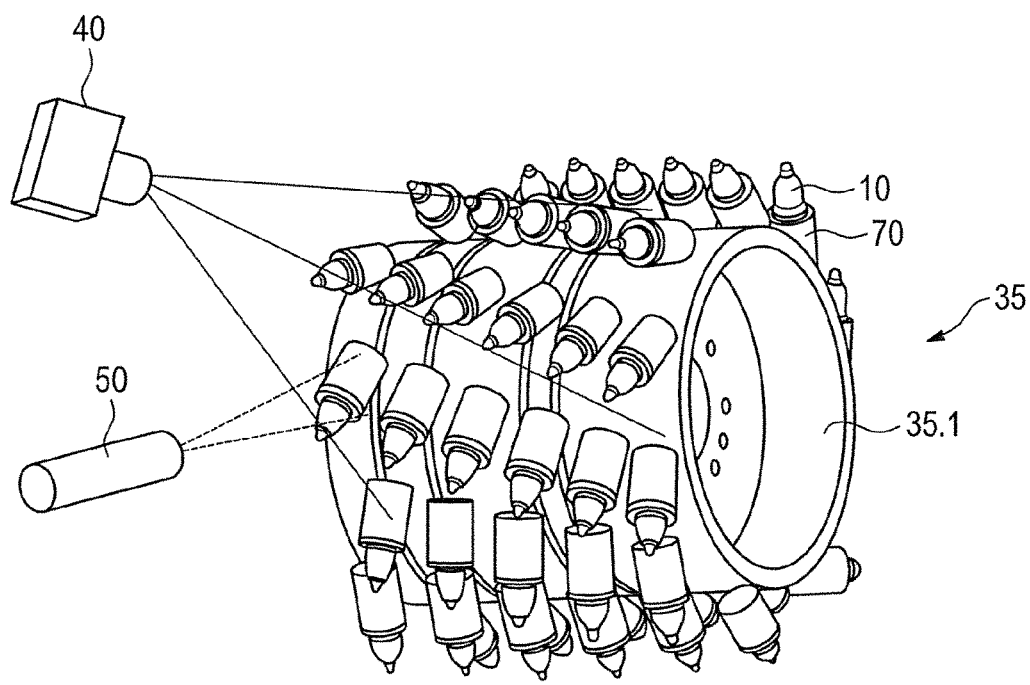
FIG. 9 shows a milling drum of the milling machine in accordance with FIG. 8, having an example of a surveying device based on the triangulation principle.

Surveying of a milling drum 35 (see FIGS. 9 and 10) can be performed when bit 10 is in the unworn, worn-out, or partly worn state. These points, the calculated bit head contour, or even only a single measurement point can then be acquired and stored as a reference value in a memory unit.

Figure 3:
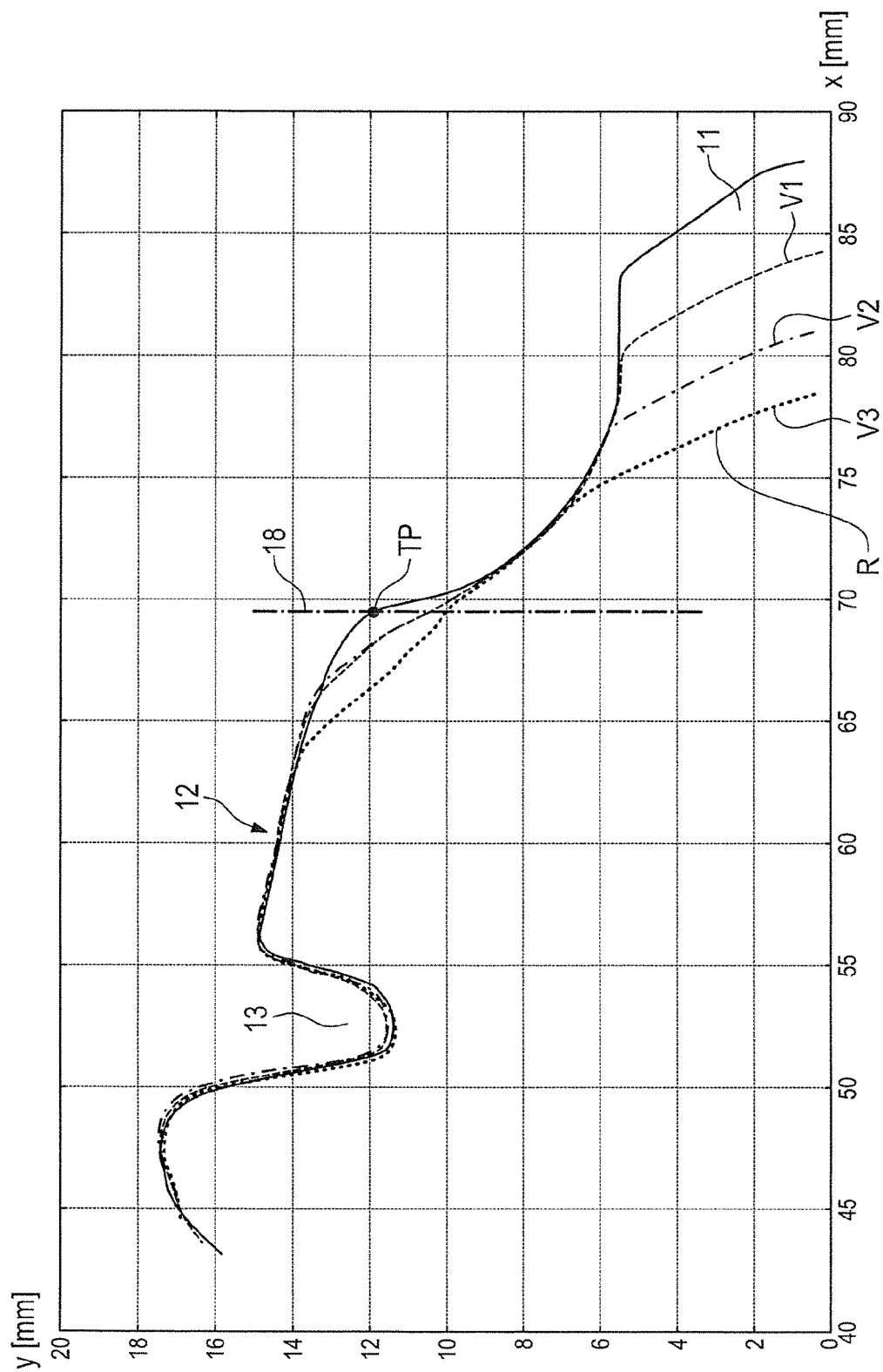
FIGS. 3 to 7 are diagrams showing various wear states of the bit head.

FIG. 3 shows a variety of measured images of a bit 10, bit head 12 being depicted in the unworn state and in three measured wear states V1 to V3. Wear state V3 represents the state in which bit 10 is no longer suitable for further processing and must be replaced. The wear can be ascertained by comparing the reference value (contour in the unworn state) with the respectively measured current bit head contour (wear states V1, V2, or V3) that reproduce the position value.

The contours must be aligned with one another. Because of holder wear or other error sources, unworn contour regions are not necessarily located at the same absolute positions (or relative positions with respect to the drum rotation axis). In order to correlate the contours there is a further need for reference features that are uniquely identifiable, occur in the unworn and worn state, and thus permit alignment and conclusive evaluation. Pull-out groove 13, wear markings 74, wear protection washer 20, or other salient regions that are subject to little or no wear can serve as reference features.

As illustrated by FIG. 3, the length of bit head 12 decreases during operational use. By differentiating the contour lines in a circuit unit it is possible to generate a statement regarding the wear state, which can be made visible to the user, for example, in a display unit. Instead of surveying the entire contour of bit head 12, it is also possible to sense only a portion of the contour or a single point, in particular the front end of bit tip 11, as a position value. Further detail in the wear statement can be achieved if the wear on bit tip 11 and on bit head 12 (without bit tip 11) is sensed separately.

This can easily be done using the position (attachment point TP/attachment line 18), known a priori, at which bit tip 11 attaches to bit head 12 in the unworn state.

Figure 4:
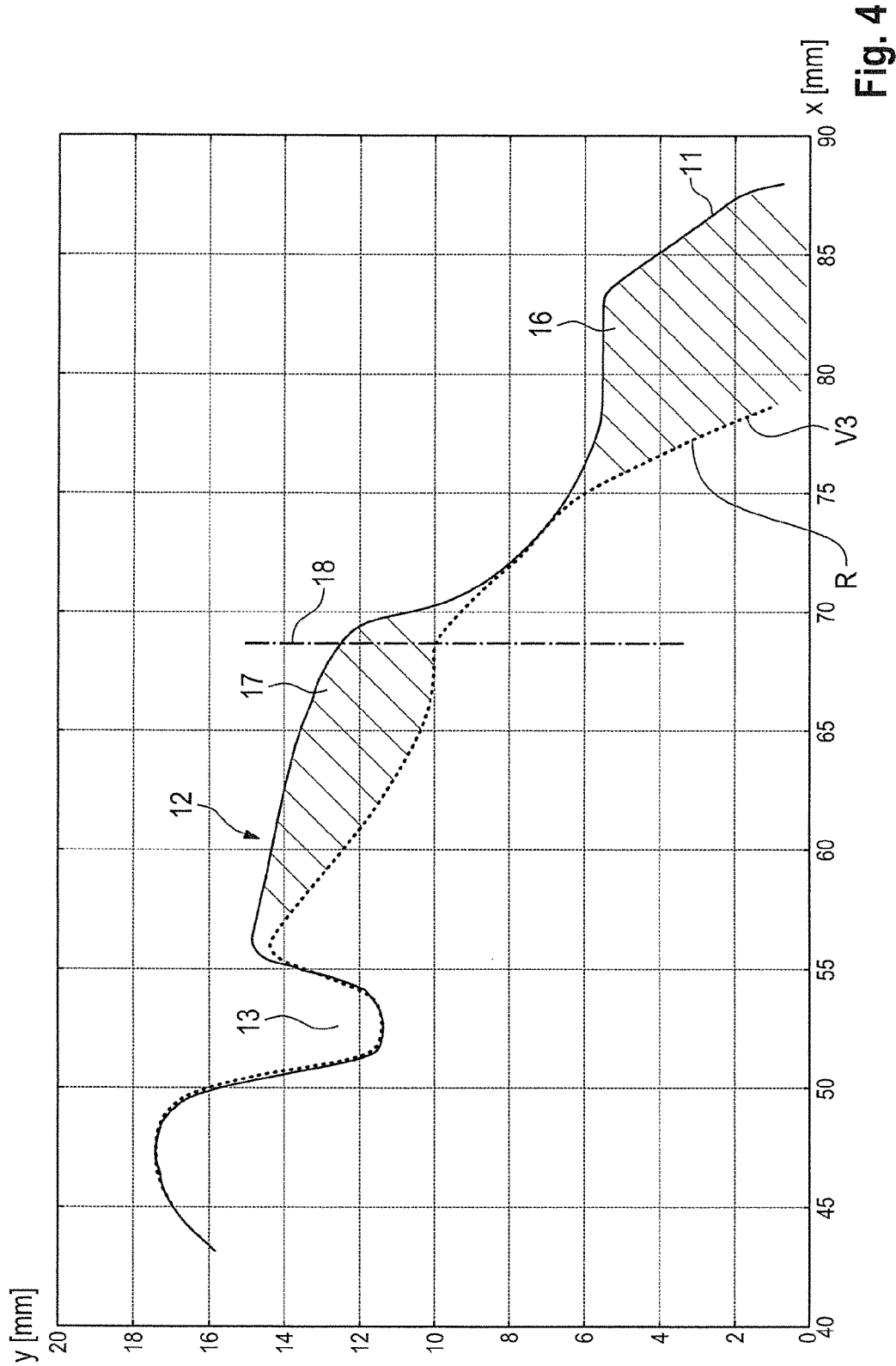

When the measured wear states V1 to V3 are overlaid on the unworn contour of bit head 12, as shown in FIG. 2, it is then possible to ascertain the total wear volume by integrating the measured contours along the X axis. In FIG. 4 the wear volume is shown as hatched areas.

The wear volume that constitutes a position value can thus be compared with a reference value. The reference value can be constituted by a functional relationship or a characteristics diagram, different wear volumes being correlated with associated wear states (for example, A mm³ of wear volume corresponds to B% wear). From the position, known a priori, of attachment point TP/attachment line 18, the tip wear 16 and head wear 17 can then also be separately ascertained by differentiation. This wear detection process provides the user, for example, with a qualitative statement as to whether bit 10 is still suitable for specific milling tasks. For example, a bit that has not yet reached its wear limit but exhibits some tip wear can no longer be used, for example, for precision milling work.

In the method according to FIGS. 3 and 4, the measured position values are overlaid on the reference values. During the working process, not only bit head 12 but also the bit holder becomes worn. The latter wears away in the direction of the longitudinal center axis of bit 10. Isolated identification of the longitudinal wear on the bit holder in this direction can now easily be achieved by the fact that the magnitude of the displacement of the position value toward the reference value in order obtain the overlays indicated in FIGS. 3 and 4 (shifting bit head 12 in the direction of the X axis, for example until the pull-out grooves of the individual wear states are superimposed) yields an absolute value for the wear on the bit holder. The total displacement of bit tip 11, minus said wear value, then separately indicates the bit wear.

Figure 5:
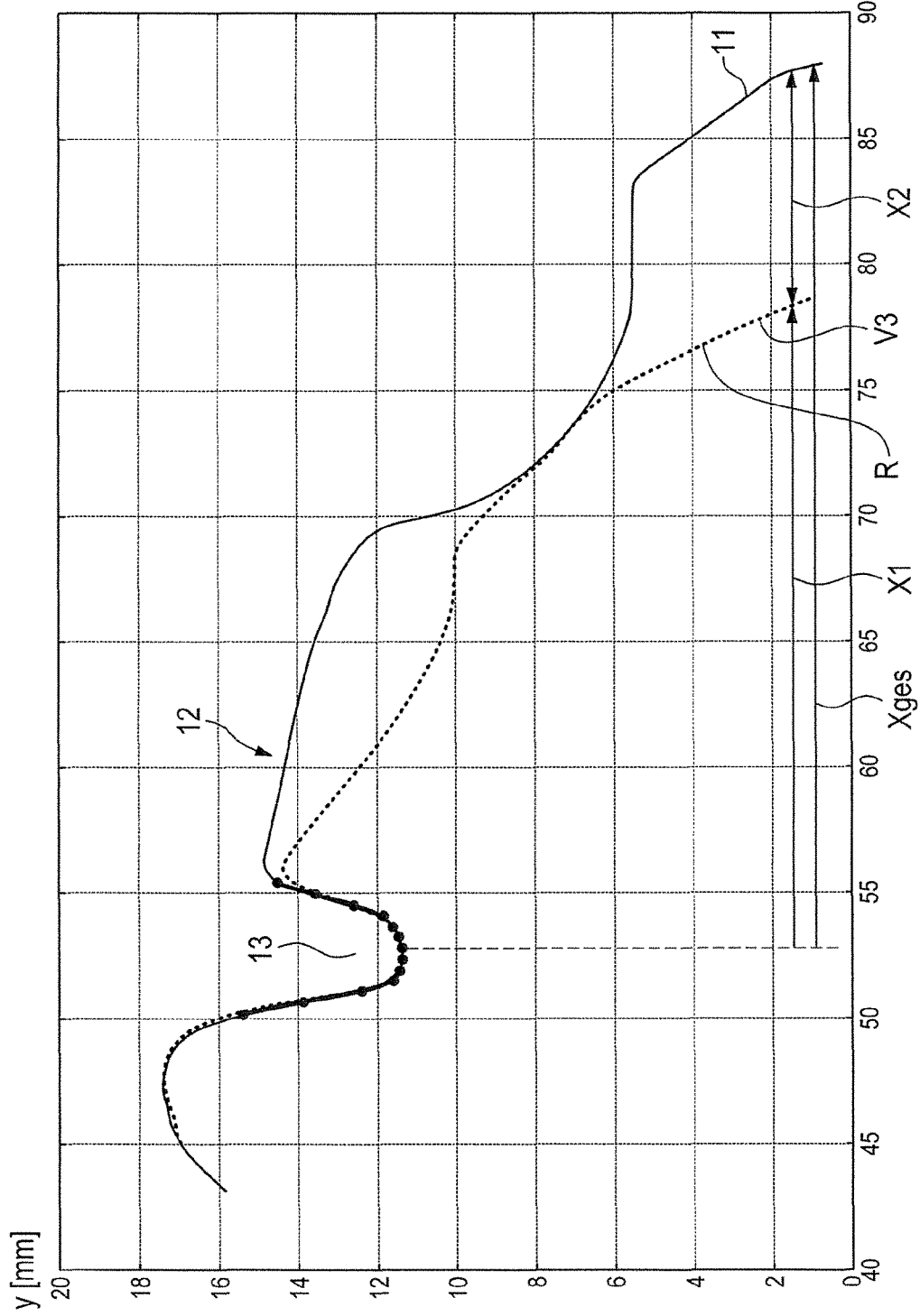

FIG. 5 shows a variant method in which a wear statement is arrived at based on surveying one uniquely identifiable feature on the bit. The feature, or the surroundings of said feature, should be subject to little or no wear. According to FIG. 5, pull-out groove 13, a portion of pull-out groove 13, or a point (for example the groove base) on pull-out groove 13 is used as a unique feature and reference criterion.

The distance from this feature to the position of the free end of bit tip 11 (position value) is then further ascertained. It is then easy to ascertain the longitudinal wear in this manner. If the position of bit tip 11 is known, then once again, as described above, the bit holder wear can also be identified. Alternatively or additionally, as defined in FIG. 4, the wear volume and the associated wear lengths—$X_1$ (currently measured length of partly worn bit), $X_2$ (worn-out length), and Xges (total length of unworn bit)—can also be ascertained.

Relative measurement using a uniquely identifiable feature as reference point has the advantage that wear detection can be performed even when a reference measurement is not available, for example because the length of the replaced bit 10, or the wear state of bit 10 or of the bit holder, is not known.

Figure 6:
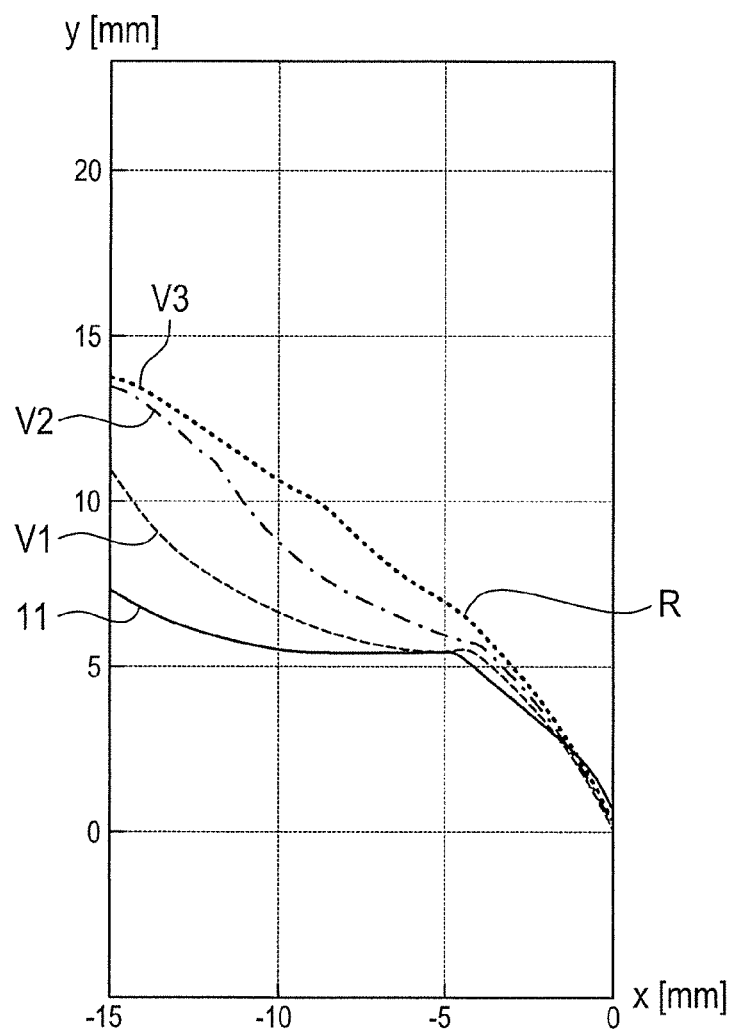

FIG. 3 shows the change in the bit head contour as wear proceeds. The decreasing length of bit head 12 is evident. If the measured bit head contours are respectively shifted to the point of the maximum length of bit 10 (FIG. 6), the increasing wear state of bit 10 is evident on the one hand from the change in head angle (the angle becomes flatter as bit wear increases) and on the other hand from the increasing volume of bit head 12 when the area under the contour curve is integrated from the respective tip over a specific length. A functional relationship can thus be created between the head volume/area and the absolute bit length for a specific bit type, for example by means of experiments carried out a priori in order to ascertain the reference values.

Once this relationship is known, the length of bit 10 can be ascertained by measurement/integration of the respectively current head volume. This method requires, however, that bit tip 11 have a cross section that increases in the longitudinal direction of the bit. The integration path is preferably defined so that integration does not occur into the head region even for completely worn-out bits 10, since head erosion distorts the result.

This method has the advantage of not requiring a reference point that is subject to little wear. Such a reference point sometimes is not present or is very difficult to identify.

Figure 7:
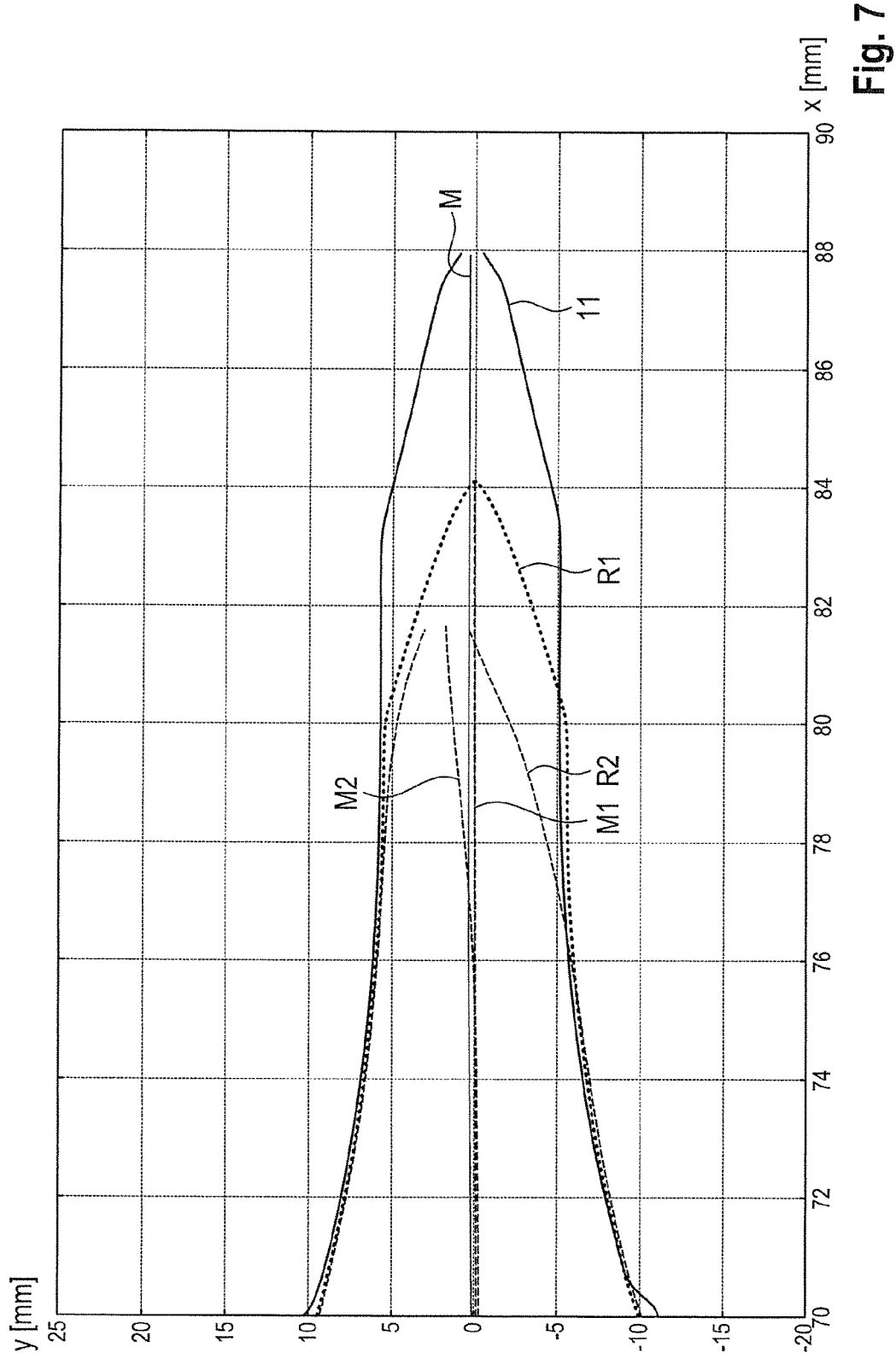

The average between the upper and lower contour line can, for example, be calculated in order to identify the degree of wear asymmetry. FIG. 7 shows the contour lines, and their averages, for a new bit tip 11 and for one that is worn rotationally symmetrically (R1) and rotationally asymmetrically (R2). It is evident that with the asymmetrically worn bit 10, the center line M2 of the two contour lines exhibits a certain slope with respect to the longitudinal bit axis. The angular position could easily be evaluated in order to determine the degree of wear asymmetry. The location/deviations of several contour lines could, however, also be identified/ascertained directly.

Asymmetrical wear on bit head 12 can be identified using the same method. Usually, however, an asymmetrically worn bit tip 11 will be accompanied by an asymmetrically worn bit head 12. An analysis of bit tip 11 is thus sufficient.

Figure 8:
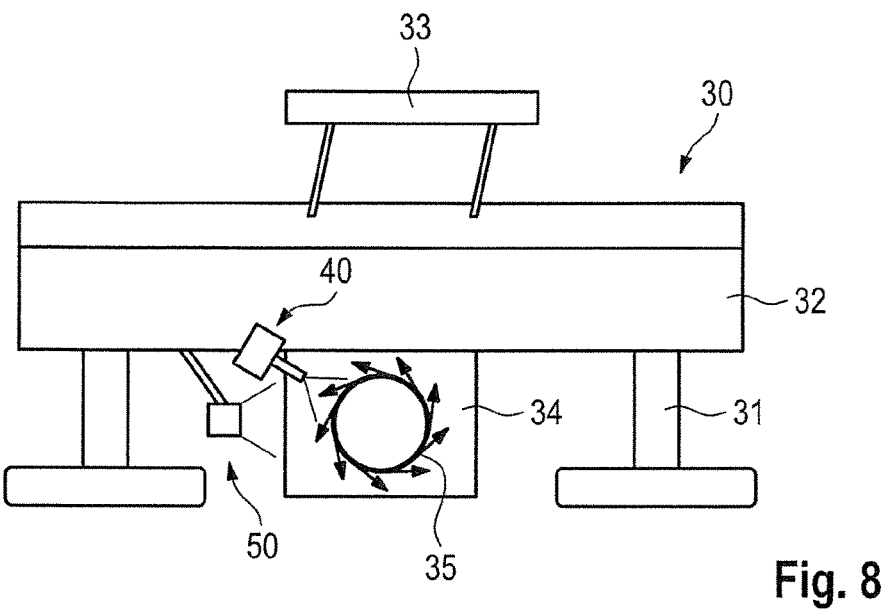
FIG. 8 is a schematic depiction and side view of a milling machine.

FIG. 8 symbolically depicts a milling machine 30, for example a surface miner, a road milling machine, or the like, in which a machine body 32 is carried by four columnar drive units 31. Road milling machine 30 can be operated from a control station 33. A milling drum 35 is arranged in a milling drum box 34.

In order to measure the wear state according to one of the methods described above, a light source 50 and a camera 40 are associated with milling drum 35. Milling drum 35 is shown more clearly in FIG. 9. A plurality of bit holder quick-change systems, each having a bit holder 70, are mounted on the surface of a milling tube 35.1 of milling drum 35. A bit 10 is held in each bit holder 70. In the present example, bit holders 70 are welded directly onto milling drum 35.

It is also conceivable, however, to use the quick-change bit holder system according to FIG. 1, in which case base part 80 is then welded onto milling drum 35.

An optical system, in which an elevation line of the drum surface is respectively surveyed in a kind of "scanning" operation, is used as an apparatus for surveying the bit contours. The measurement principle that can be used here is, for example, a triangulation method in which the drum surface is illuminated, for example, by a light source 50, for example a laser line. When the laser line thereby generated is observed by a camera 40 at a different angle, elevation differences on the drum surface (caused, for example, by bits 10) are evident as shifts of these projection lines. If the angular difference between camera 40 and light source 50 is known, the elevation coordinates can be calculated. By rotating milling drum 35 it is thus possible to create an elevation profile of the drum's enveloping surface, from which profile the contour line of the individual bits 10 can then be read out. A further optical measurement principle for surveying the elevation and/or geometry of bits 10 is the shadow-casting method according to FIG. 10. This method makes use of the fact that bits 10 moving through a light curtain generated by a light source 50 generate a shadow contour that can be observed and evaluated by a camera 40. The great advantage of this method lies in the fact that it is possible to work with a single camera row, in principle like a document scanner. This means that, in particular, even milling drums 35 having a large diameter and high rotation speeds can be surveyed with sufficient resolution.

Figure 10:
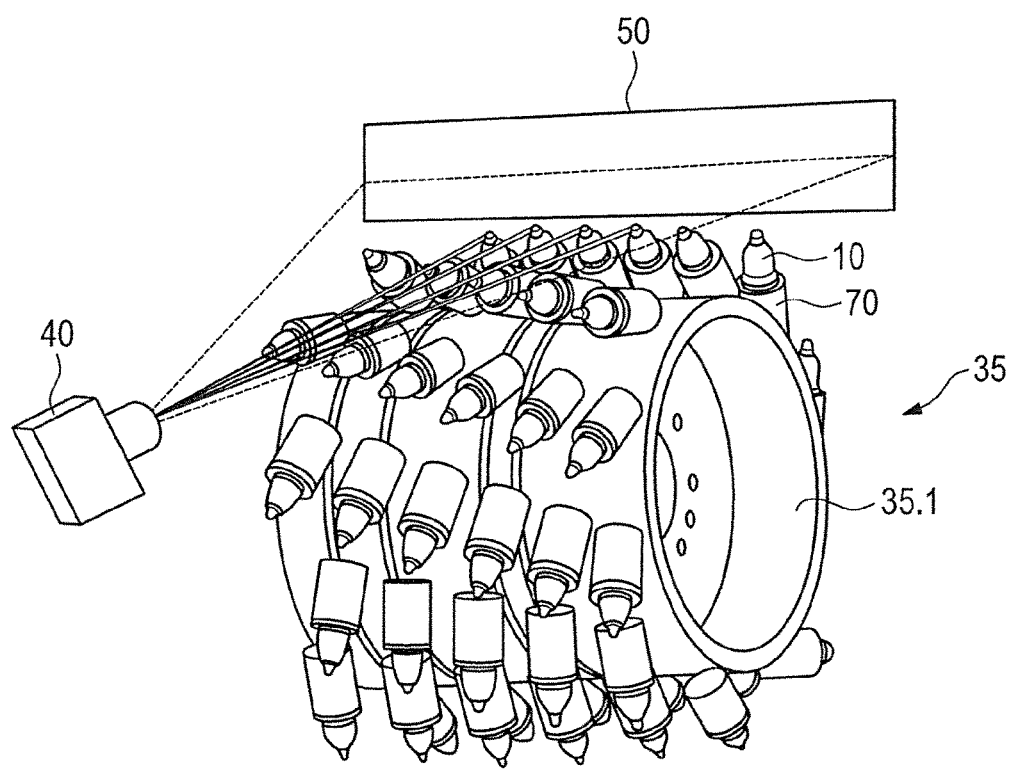
FIG. 10 shows the milling drum in accordance with FIG. 8, having an alternative embodiment of the surveying device based on a shadow-casting method.

The method described with reference to FIG. 10 can be modified in accordance with an alternative variant embodiment of the invention. Here once again a light curtain in the form of a light plane is generated using a light source 50. This light plane extends parallel to the longitudinal center axis of milling drum 35 and tangentially to the drum surface. The light plane is configured so that in the case of a rotating milling drum 35, the tips of bits 10 are the first to penetrate through the light plane.

They then cast a shadow that can be sensed by camera 40. Bits 10 are guided through the light plane over a specific drum rotation angle until they then sink again below the light plane.

A reference measurement can be performed with unworn bits 10/bit holders 70. Here the time at which bit 10 passes through the light plane (entry or exit) is sensed, and the associated rotation angle of milling drum 35 is sensed. After operational use, a corresponding measurement is then performed on the partially worn (worn out) bit 10. Because of the reduced length as compared with an unworn system, bit 10 passes through the light plane at a later time, and sinks below it sooner. The corresponding rotation angle of milling drum 35 can then be ascertained as a position value. These rotation angles are then compared with the rotation angles for the unworn system (reference value). A calculation of the wear state can then be made from the angle difference by differentiation, or the rotation angle difference is employed directly as a wear criterion.

During the milling process, for example in phases during which measurement does not occur, the measurement system is usefully stowed in a corresponding protective apparatus. If a second camera 40 is used, for example, direct surveying of the elevation geometry can be performed without an additional illumination source.

Alternatively, by correspondingly placing a second camera, additional measurements of the contours can be carried out so that the overall information density is increased and the detection probability for asymmetrical wear states is raised.

Alternatively, the position of bit tip 11 or the location of the bit head contour can also be sensed in at least one step using other sensor equipment that measures distance (e.g. ultrasonic sensors, proximity switches).

As already explained in detail above, the following can be ascertained using the measurement methods described above:
1. The current wear state $V_1, V_2, V_3$ of an earth working tool (bit 10),
2. The wear resulting from comparison of a reference value (bit 10 in the unworn or partially worn state) with the current wear state $V_1, V_2, V_3$.

In order for the wear according to item 2. above to occur, the earth working machine must have produced a certain milling output. This milling output can be measured, for example as a number of tons milled (milled mass), as a milled volume, and/or as a milled distance, etc. The milling output can in particular be ascertained directly on an earth working machine. If the earth working machine is equipped with a measurement system described above, the wear (see 2.) can also be sensed directly and the characteristic value or values can be derived in conjunction with the ascertained milling output.

Based on the measured current wear state V1, V2, and with a knowledge of the wear limit V3 of bit 10, the residual wear capacity of bit 10 can now be ascertained. For example, if the measured free end of bit tip 11 according to FIG. 5 represents the current wear state constituting a position value, the distance to the reference contour R reproducing the wear state, and thus the residual wear length (Xges—X1), can thus be ascertained as the residual wear capacity by differentiating in the X axis direction. Additionally or alternatively, the residual wear capacity can be ascertained as the residual wear volume of bit tip 11 remaining until the wear limit V3 is reached. This is done, for example (see discussion above of FIG. 4), by overlaying the measured wear state V1, V2 of the bit contour on the reference contour R in the worn state V3. The residual wear volume can then be ascertained by integration along the X axis.

The change in wear state is influenced by material properties, for example by the hardness and/or abrasiveness of the milled material. The material properties can be sensed indirectly. For example, samples can be taken (e.g. sample boring operations) in the area to be milled, and can be evaluated.

It is also conceivable to use existing mining category systems. General hardness and abrasiveness categories are defined for mines (e.g. "hard, non-abrasive," "moderate, non-abrasive," "soft, abrasive," etc.). From these categories, the category matching the planned route of travel can be selected.

The material properties can also be ascertained by evaluating machine data (e.g. rotation speed of the milling drum, torque, advance, and milling depth), since the material properties correlate directly with these machine data.

Characteristic values can be ascertained as a function of the milling output and/or the material properties. These characteristic values indicate the change in the wear state which is to be expected for a specific milling output and/or for predefined material properties.

Based on the residual wear capacity and in consideration of one or more characteristic values, the remaining working output can then be signaled to the machine operator. He can be informed, for example, as to the milling output that can still be produced (e.g. mass or volume of material that can still be milled, number of truckloads that can still be milled, travel distance that can be milled, or milling time).

If the milling output per unit time for an earth working machine is known, it is also possible in particular to indicate the time remaining until the next tool change. The milling output per unit time can be continuously ascertained on the basis of current machine parameters (advance, milling depth). It can also be previously known based on milling work already carried out at the same location.

Figure 11:
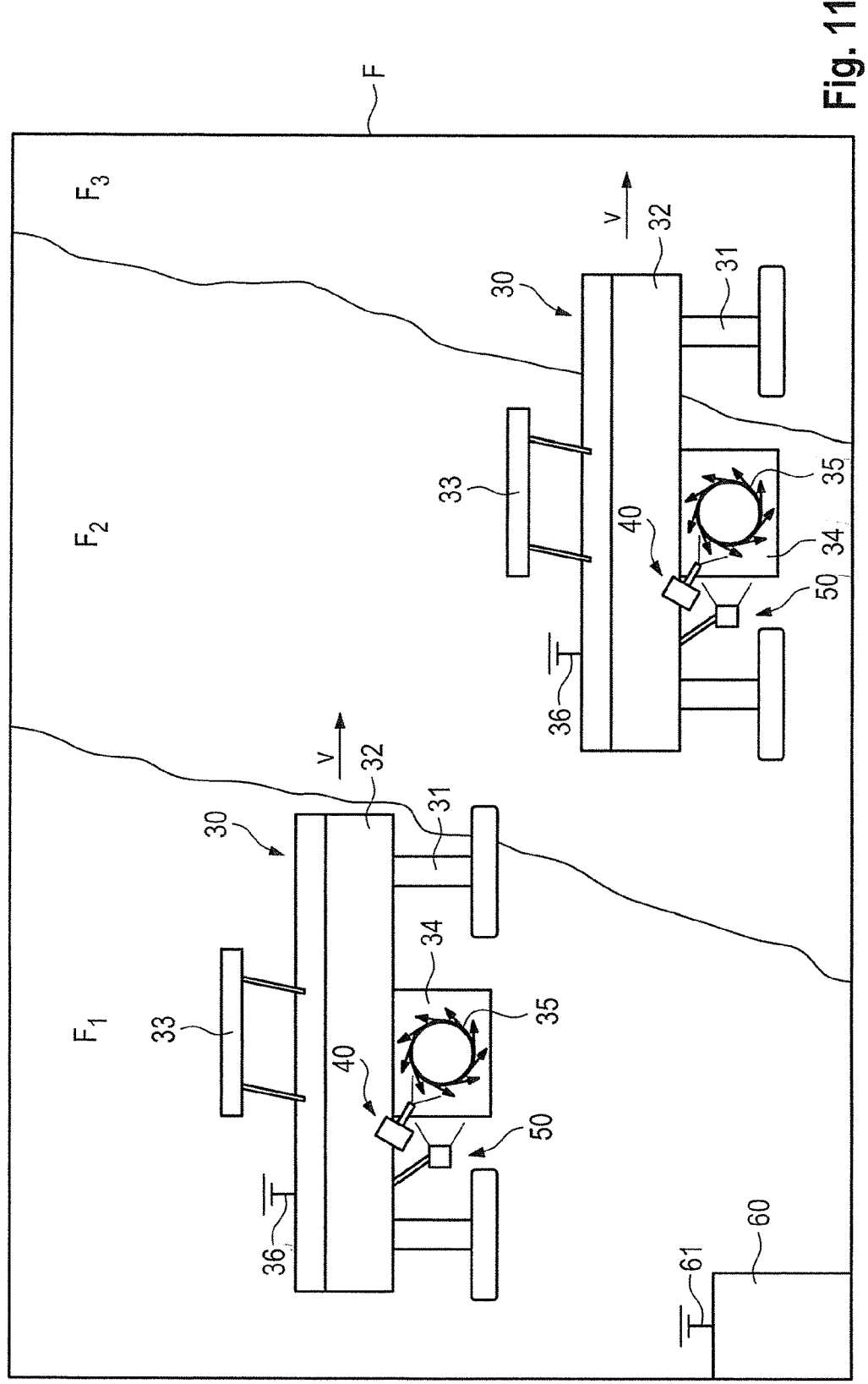
FIG. 11 schematically depicts a working situation with two milling machines.

FIG. 11 illustrates a milling area F, for example a mine, in which multiple milling machines 30 are working. Milling area F contains a raw material deposit, and the material properties change in sub-areas $F_1$, $F_2$, $F_3$.

These sub-areas $F_1$, $F_2$, $F_3$ are associated in mine maps with hardness and abrasion categories (see above). Before work begins, the measurement system (for example, camera 40) ascertains the current wear state $V_1$, $V_2$ and conveys this, as well as the current position of the machine, via a transmission and reception apparatus 61 to an external system unit 60. There, in consideration of the calculated residual wear capacity and of one or more characteristic values, the remaining milling output until the wear limit V3 is reached is ascertained. The characteristic value ideally takes into account the planned route of travel and the various hardness and abrasion categories, associated therewith, in sub-areas $F_1$, $F_2$, $F_3$, as well as the expected wear related to the hardness and abrasion categories. The ascertained working output until the wear limit V3 is reached is signaled back to milling machine 30.

Milling machine 30 depicted on the right in FIG. 11 has already traveled over sub-areas $F_1$ and $F_2$ and has acquired measured values in that context. These measured values can be evaluated. For example, it is possible to sense what kind of wear occurs with what milling output. This result, or the characteristic values resulting therefrom, can then be respectively made available to the second milling machine in FIG. 11 in order to improve the quality of the wear prognosis.

The invention claimed is:

1. A method of determining wear for an earth working machine having at least one earth working tool, the method comprising:

prior to an earth working operation of the earth working machine:
sensing one or more position values corresponding to a current tool contour of the at least one earth working tool;
determining a first wear state by comparing the one or more position values of the current tool contour with a reference tool contour aligned therewith; and
during the earth working operation of the earth working machine:
continuously determining an actual work output of the earth working machine from one or more machine parameters;
determining a second wear state of the at least one earth working tool, based on a calculated change in wear from the first wear state corresponding to the continuously determined actual work output and a material property of a corresponding substrate worked since beginning the earth working operation;
predicting a remaining work output until a third wear state of the at least one earth working tool, based on an expected change in wear from the second wear state corresponding to a material property of a substrate yet to be worked during the earth working operation.

2. The method of claim 1, wherein the at least one earth working tool includes a bit and/or a bit holder.

3. The method of claim 1, wherein the remaining work output for the earth working machine is determined in terms of at least one of:
a milling output of the earth working machine;
a mass of material to be milled by the earth working machine;
a volume of material to be milled by the earth working machine;
a remaining travel distance for the earth working machine; and
a remaining working time for the earth working machine.

4. The method of claim 1, during the earth working operation further comprising:
continuously determining the material property of the substrate being worked by the earth working machine, and
reading out at least one characteristic value from a database, said characteristic value derived from the determined material property and corresponding to a change in the wear state which is expected for a given work output in the substrate to be worked.

5. The method of claim 4, further comprising:
identifying a working area within which two or more earth working machines are being used,
wherein a characteristic value for the first one of the earth working machines is derived from a previously produced work output of the first one of the earth working machines and a change in wear state of the at least one earth working tool of the first one of the earth working machines corresponding to the previously produced work output; and
wherein the characteristic value for the first one of the earth working machines in the working area is used to determine a remaining work output for a second one of the earth working machines in the working area.

6. The method of claim 4, wherein the at least one characteristic value corresponds to a material hardness range including a material hardness of a substrate to be worked by the earth working machine.

7. The method of claim 4, wherein the at least one characteristic value corresponds to an abrasiveness range including an abrasiveness of a substrate to be worked by the earth working machine.

8. The method of claim 4, further comprising determining the at least one characteristic value based on one or more machine parameters observed during operation of the earth working machine, the one or more machine parameters being selected from the group consisting of:
   milling depth;
   advance speed;
   milling drum rotation speed;
   torque currently applied to a milling drum; and
   power output currently being delivered by a drive engine.

9. The method of claim 4, wherein the at least one characteristic value is stored in a memory of the controller, and the controller determines the remaining work output of the earth working machine based upon the second wear state and the at least one characteristic value.

10. The method of claim 9, wherein the controller and the memory are located on the earth working machine.

11. The method of claim 9, wherein the controller and the memory are located in a separate control system separate from the earth working machine.

12. The method of claim 11, wherein the earth working machine and the separate control system are in mutual communication via a wireless remote data transfer link.

13. The method of claim 1, further comprising:
   determining a second wear state for each of a plurality of earth working tools of the earth working machine; and
   determining a remaining work output for the earth working machine based upon each one of the plurality of earth working tools having at least a threshold residual wear capacity.

14. The method of claim 1, further comprising:
   before the third wear state of the at least one earth working tool is reached, informing a technician that tool maintenance is needed.

15. The method of claim 14, wherein the step of informing a technician includes wirelessly conveying a signal to the technician from the earth working machine or from a control system separate from the earth working machine.

16. The method of claim 14, further comprising signaling the remaining work output in terms of at least one of:
   a distance that can still be milled by the earth working machine;
   a volume that can still be milled by the earth working machine;
   a mass that can still be milled by the earth working machine; and
   a remaining service life of the earth working machine.

17. The method of claim 14, further comprising:
   planning a working process; and
   determining maintenance intervals for the earth working machine as a function of predicted remaining work output for each of a plurality of earth working tools as a function of the planned working process.

* * * * *